(12) United States Patent
Kilduff et al.

(10) Patent No.: US 9,943,444 B2
(45) Date of Patent: Apr. 17, 2018

(54) GOGGLE SYSTEM AND METHOD

(71) Applicant: BERN UNLIMITED INC., Kingston, MA (US)

(72) Inventors: Matthew Kilduff, Greenbush, MA (US); Marc Tappeiner, Santa Barbara, CA (US)

(73) Assignee: Portal Instruments, Inc., Cambridge, MA (US)

( * ) Notice: Subject to any disclaimer, the term of this patent is extended or adjusted under 35 U.S.C. 154(b) by 168 days.

(21) Appl. No.: 15/147,995

(22) Filed: May 6, 2016

(65) Prior Publication Data

US 2016/0331591 A1    Nov. 17, 2016

Related U.S. Application Data

(60) Provisional application No. 62/162,259, filed on May 15, 2015.

(51) Int. Cl.
*A61F 9/02*    (2006.01)

(52) U.S. Cl.
CPC .............. *A61F 9/025* (2013.01); *A61F 9/027* (2013.01); *A61F 9/028* (2013.01)

(58) Field of Classification Search
CPC .......... A61F 9/025; A61F 9/026; A61F 9/027; A61F 9/028; A61F 9/029; A61F 9/02; A61F 2009/022; A42B 3/22; A42B 3/221; A63B 33/002; B63C 11/12
USPC .................... 2/434, 436, 452, 429, 441, 443
See application file for complete search history.

(56) References Cited

U.S. PATENT DOCUMENTS

| | | | |
|---|---|---|---|
| 3,517,393 A | 6/1970 | Beauchef | |
| 3,718,937 A * | 3/1973 | Smith | A61F 9/025 2/436 |
| 4,689,838 A | 9/1987 | Angermann et al. | |
| 5,363,512 A * | 11/1994 | Grabos, Jr. | A61F 9/028 2/436 |
| 6,092,243 A * | 7/2000 | Wu | A61F 9/025 2/426 |
| D537,100 S | 2/2007 | Moritz et al. | |
| 7,810,174 B2 | 10/2010 | Matera | |
| D629,034 S | 12/2010 | McNeal et al. | |
| D629,035 S | 12/2010 | Moritz et al. | |
| D649,178 S | 11/2011 | Moritz et al. | |
| D657,812 S | 4/2012 | Li | |
| D673,206 S | 12/2012 | Abdollahi et al. | |
| D678,932 S | 3/2013 | Moritz et al. | |
| D687,881 S | 8/2013 | Ginther et al. | |
| D695,818 S | 12/2013 | Laperriere et al. | |
| D715,350 S | 10/2014 | Moritz et al. | |
| D718,369 S | 11/2014 | Janavicius et al. | |
| 8,881,316 B2 * | 11/2014 | Reyes | A61F 9/025 2/431 |
| 2006/0179554 A1 * | 8/2006 | Barton | A61F 9/026 2/426 |
| 2007/0153230 A1 * | 7/2007 | Musal | A61F 9/025 351/142 |
| 2008/0155736 A1 * | 7/2008 | Paulson | A61F 9/025 2/441 |

(Continued)

*Primary Examiner* — Amy Vanatta
(74) *Attorney, Agent, or Firm* — Lando & Anastasi, LLP

(57) ABSTRACT

A pair of goggles includes a flexible body, a lens assembly, and a quick release system configured to removably couple the lens assembly to the flexible body.

22 Claims, 17 Drawing Sheets

(56) References Cited

U.S. PATENT DOCUMENTS

| | | | | |
|---|---|---|---|---|
| 2008/0256688 A1* | 10/2008 | Bruce | ............... | A61F 9/025 2/441 |
| 2009/0019620 A1 | 1/2009 | Reed | | |
| 2011/0225709 A1* | 9/2011 | Saylor | ............... | A61F 9/025 2/431 |
| 2012/0137398 A1* | 6/2012 | Arnold | ............... | A61F 9/025 2/10 |
| 2012/0324638 A1* | 12/2012 | Tobia | ............... | A61F 9/02 2/439 |
| 2013/0097855 A1* | 4/2013 | Li | ............... | A61F 9/025 29/700 |
| 2014/0157496 A1* | 6/2014 | Ginther | ............... | A61F 9/025 2/439 |
| 2015/0290038 A1* | 10/2015 | Wang-Lee | ............... | A61F 9/029 2/439 |

* cited by examiner

GOGGLE SYSTEM AND METHOD

CROSS-REFERENCE TO RELATED APPLICATION

This application claims the benefit of priority under 35 U.S.C. § 119(e) to U.S. Provisional Patent Application Ser. No. 62/162,259 titled "GOGGLE SYSTEM AND METHOD" filed on May 15, 2015, which is hereby incorporated herein by reference in its entirety for all purposes.

BACKGROUND

1. Technical Field

Aspects and embodiments of the present invention are directed generally to protective goggles, and more specifically to protective goggles having features rendering the goggles desirable for use in sporting activities, for example, skiing, motorcycle riding, and paint-ball games.

2. Discussion of Related Art

Goggles are used in many sports for protecting the eyes of a wearer. Such sports may include, for example, biking, skiing, snowboarding, skydiving, motorcycle riding, and paint-ball gaming.

In some examples, a pair of goggles may include a rigid or semi-rigid shell or frame designed to provide mechanical strength and support for other components of the goggles. A strap may be affixed to the frame which, in use, is worn about the head of a wearer to retain the goggles in place on the face of the wearer. A lens, often formed from tinted plastic, may be affixed to the front of frame to protect the eyes of the wearer from, for example, snow, dirt or other debris. The lens may also protect the eyes of the wearer from bright sunlight and/or ultraviolet radiation. Padding may be provided on the rear side of the shell or frame which, in use, comes in contact with the face of the wearer. The padding may act as a perspiration barrier or blotter and may further protect the eyes of the wearer from snow, dirt or other debris.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
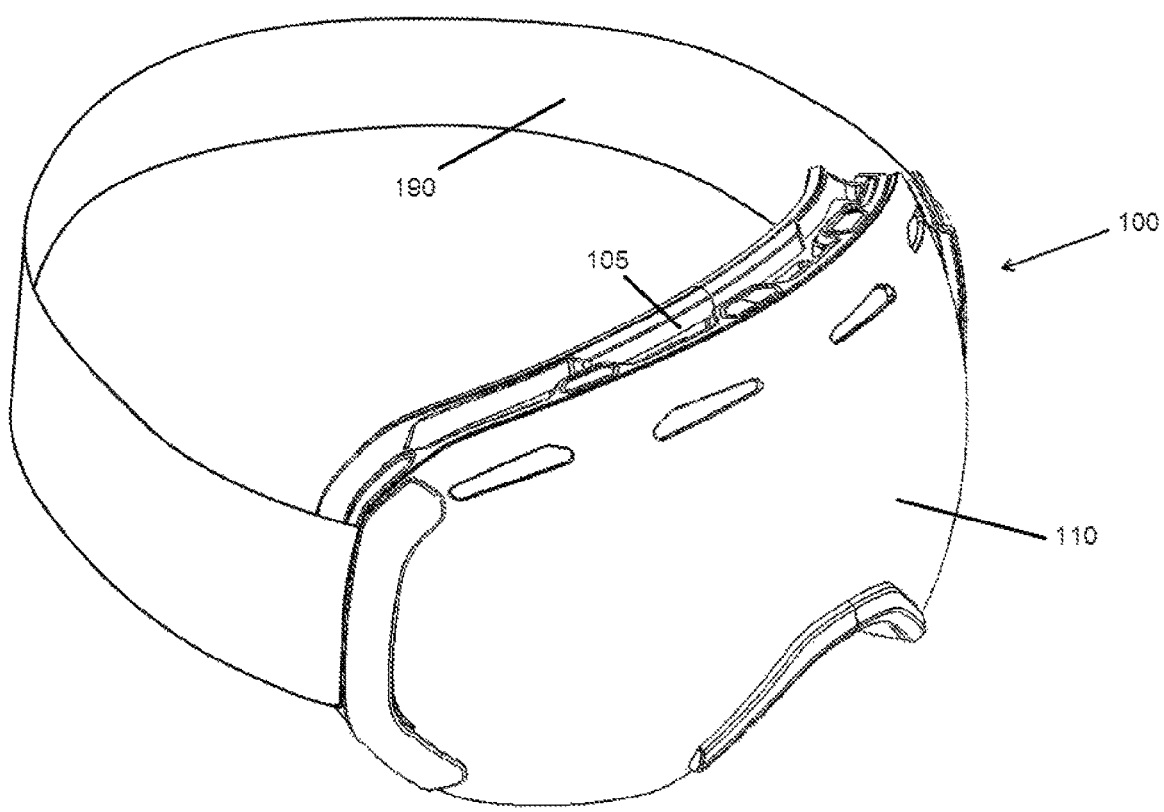
FIG. 1 is an isometric view of an embodiment of a pair of goggles.

Aspects and embodiments disclosed herein are not limited to the details of construction and the arrangement of components set forth in the following description or illustrated in the drawings. The disclosed aspects and embodiments are capable of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

The present disclosure will be described with reference to goggles designed for use in sporting activities, referred to herein synonymously as "sports goggles" or simply "goggles," although it should be understood that aspects and embodiments disclosed herein may equally apply to other forms of goggles, for example, protective goggles for use in a construction environment or a laboratory.

Aspects and embodiments disclosed herein include goggles having one or more features which provide one or more advantages relative to prior known goggles. These advantages may include, for example, greater comfort and fit, lighter weight, a ventilation system providing superior fog resistance, lens seals providing superior resistance to the passage of snow, dirt or other debris into the interior of the goggles, a simple method of reconfiguring the goggles, and a unique lens mounting system for securely mounting a lens to a frame of the goggles. Aspects and embodiments of goggles disclosed herein may be formed from recyclable materials, providing for an environmentally friendly product.

Figure 2:
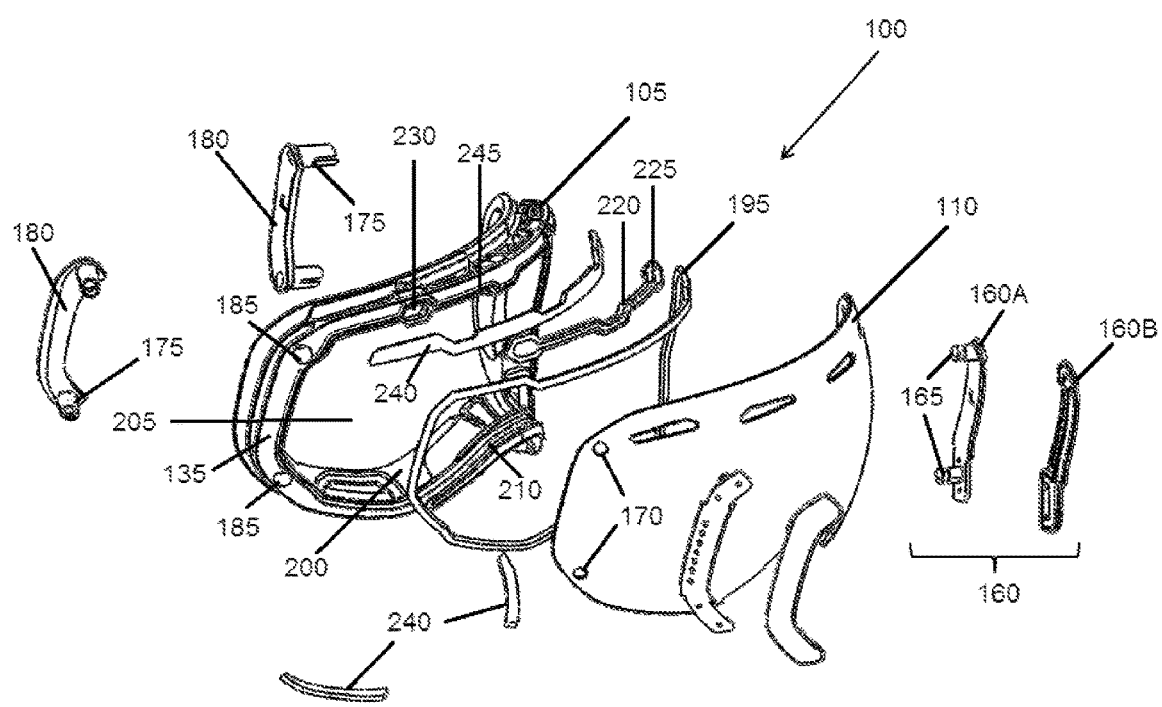
FIG. 2 is an exploded view of the goggles of FIG. 1.

In one embodiment, illustrated in isometric view in FIG. 1 and in an exploded view in FIG. 2 (with headstrap omitted for clarity), a pair of goggles 100 includes a flexible body 105 which supports a lens assembly 110 and other components of the goggles. The body 105 is flexible in the sense that it may be reversibly twisted and/or may undergo reversible compression without mechanical failure and may conform to the general shape of the face of a wearer under the influence of a force applied to the body 105 by a headstrap coupled to the body 105 and worn about the head of the wearer and may return to an original shape upon removal of the goggles 100 from the face of the wearer. The flexible body 105 is, in some embodiments, formed from a soft closed cell foam which conforms easily to the general shape of the face of a wearer. The foam may be a polymeric foam. The flexible body 105, in some embodiments, includes or consists of PLUSfoam™ recyclable foam, available from PLUSfoam Compound Technologies. The flexible body 105 may be formed from a molded foam material. The flexible body 105 may additionally or alternatively include or consist of ethylene-vinyl acetate (EVA) closed cell foam. In some embodiments, the goggles 100 are substantially lighter than conventional goggles, for example, having a weight of about 115 grams as compared to a weight of about 400 grams or more as in some examples of conventional goggles.

Figure 3:
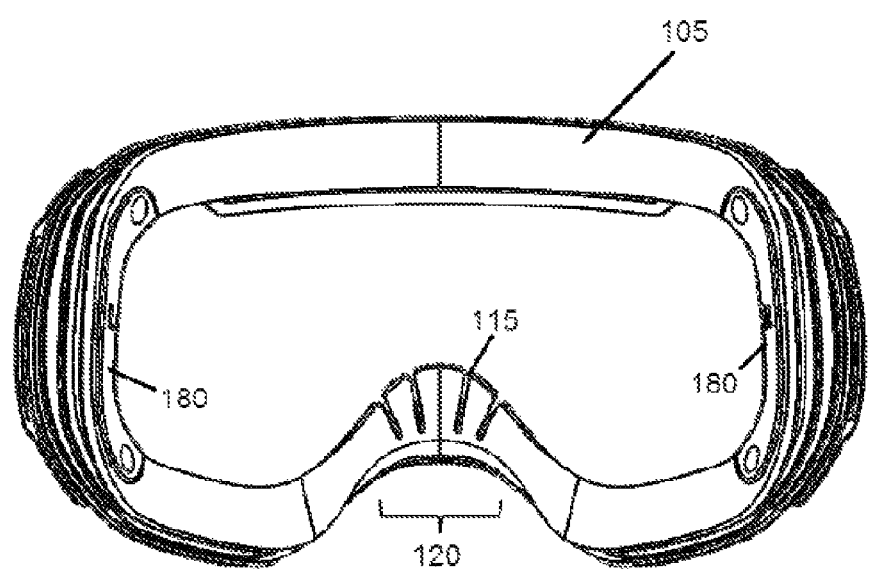
FIG. 3 is an elevation view of the rear of the goggles of FIG. 1.
Figure 4:
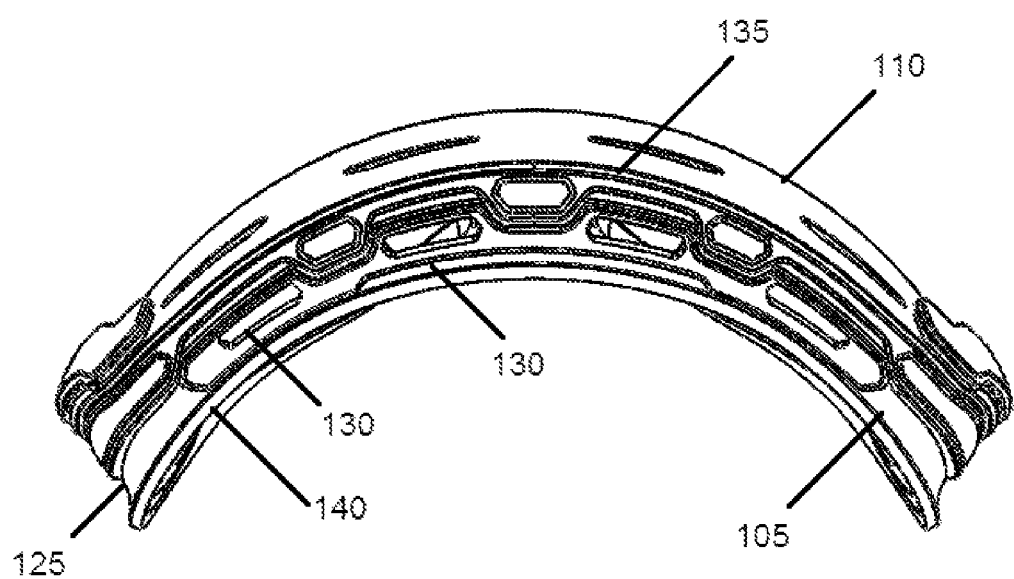
FIG. 4 is a plan view of the goggles of FIG. 1.

In some embodiments, the flexible body 105 includes one or more features to enhance the flexibility of the flexible body 105 to allow it to more easily conform to the face of a wearer and provide a better seal against the face of the wearer and a more comfortable fit. In some embodiments, the flexible body 105 includes crenels, for example, channels 115 formed in a nose bridge section 120 of the flexible body 105 (see FIG. 3) and/or recesses 125 and/or apertures 130 (see FIG. 4) to increase the flexibility of the flexible body 105. In some embodiments, the crenels may include portions of the walls of the flexible body 105 surrounding the apertures 130 that may be thinner than other portions of the walls of the flexible body 105. In some embodiments, the material of the flexible body is more rigid at a front face 135 of the flexible body 105 and more pliable at a rear face 140 of the flexible body to provide both sufficient strength at the front face 135 to reliably support the lens assembly 110 and a softer surface to facilitate conforming to the shape of a face of a wearer at the rear face 140.

Figure 5:
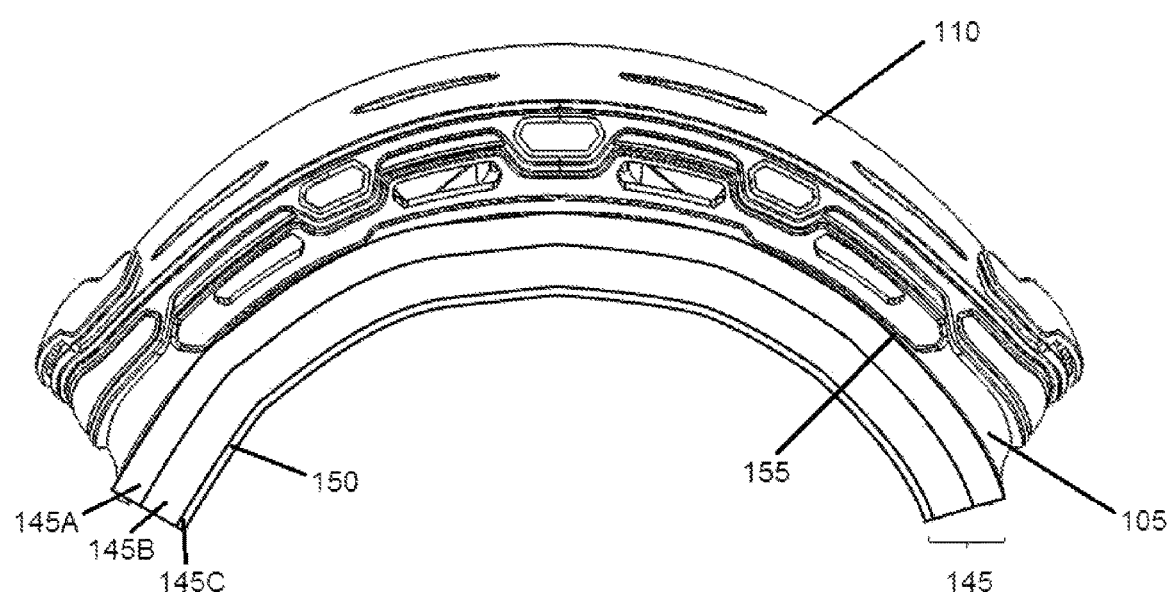
FIG. 5 illustrates an embodiment of a face foam gasket for use with the goggles of FIG. 1.

A cushioning and/or sealing element may be coupled to the rear face 140 of the flexible body 105 (See FIG. 5). For example, in some embodiments, a face foam gasket 145 is attached to the rear face 140 of the flexible body 105. The face foam gasket 145 is, in some embodiments, a soft closed cell foam that is softer than the foam of the flexible body 105. The face foam gasket 145 may include or consist of a polymeric foam, for example, a polyurethane foam. The face foam gasket 145 may be antimicrobial and may be washable. In use, the face foam gasket 145 conforms to the specific contours of the face of a wearer and forms a seal against the face of the wearer to prevent snow, dirt, or other debris from entering the interior of the goggles 100 and irritating the eyes or face of the wearer. The face foam gasket 145 may include a plurality of layers bonded together, for example, layers 145A and 145B as shown in FIG. 5. The forward layer 145A may be stiffer than the rear layer 145B to provide the face foam gasket 145 with both a relatively stiff surface to facilitate connection to the flexible body 105 and a soft rear layer 145B that facilitates conformance to the face of a wearer. A rear surface 150 of the face foam gasket 145 may be laminated with a soft, breathable fabric 145C to provide a comfortable fit on the face of the wearer.

In some embodiments, the face foam gasket 145 is reversibly detachable from the rear face 140 of the flexible body 105. The face foam gasket 145 may include, for example, hook and loop fasteners, snaps, and/or other connectors on a front surface 155 that may reversibly engage complimentary fasteners or connectors disposed on the rear face 140 of the flexible body 105. The complimentary fasteners or connectors may be counter-sunk into the rear face 140 of the flexible body 105 to help prevent gaps from forming between the rear face 140 of the flexible body 105 and the front surface 155 of the face foam gasket 145. The face foam gasket 145 may be removed from the flexible body 105, for example, to be washed, or to be replaced when damaged as desired by the wearer.

Figure 6A:
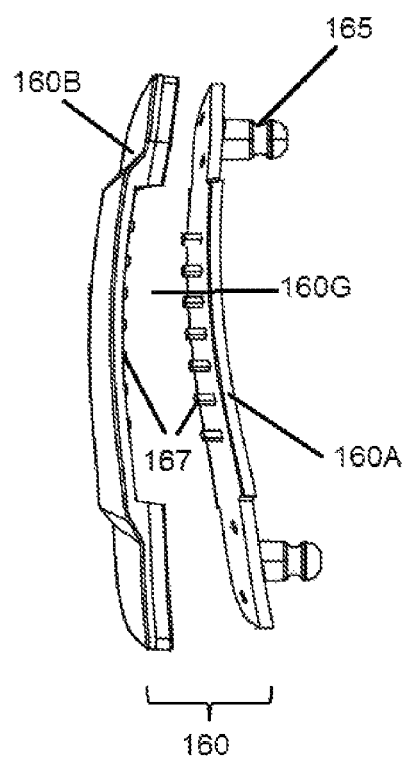
FIG. 6A is an exploded view of an outrigger assembly for use with the goggles of FIG. 1.
Figure 6B:
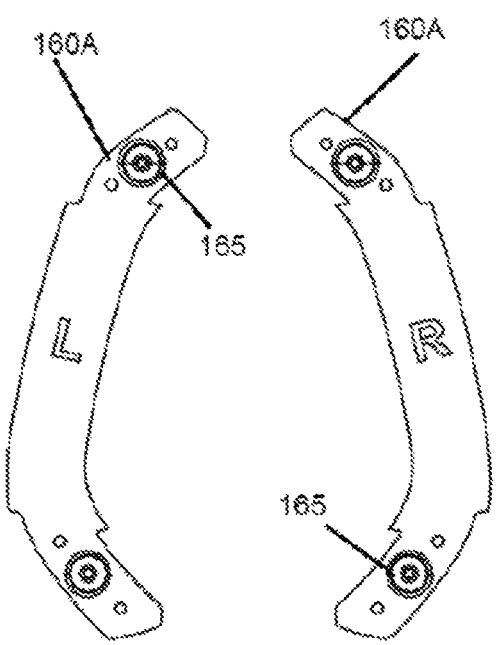
FIG. 6B is an elevational view of front sides of front portions of a pair of outrigger assemblies as illustrated in FIG. 6A.
Figure 6C:
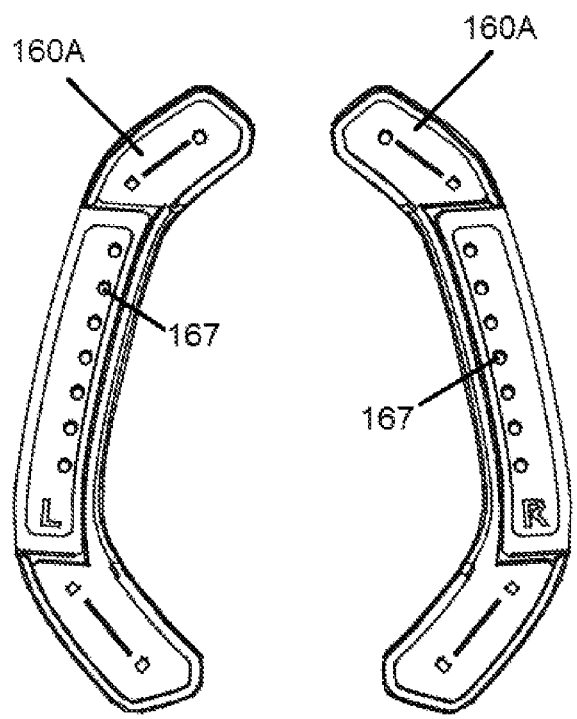
FIG. 6C is an elevational view of rear sides of front portions of a pair of outrigger assemblies as illustrated in FIG. 6A.
Figure 6D:
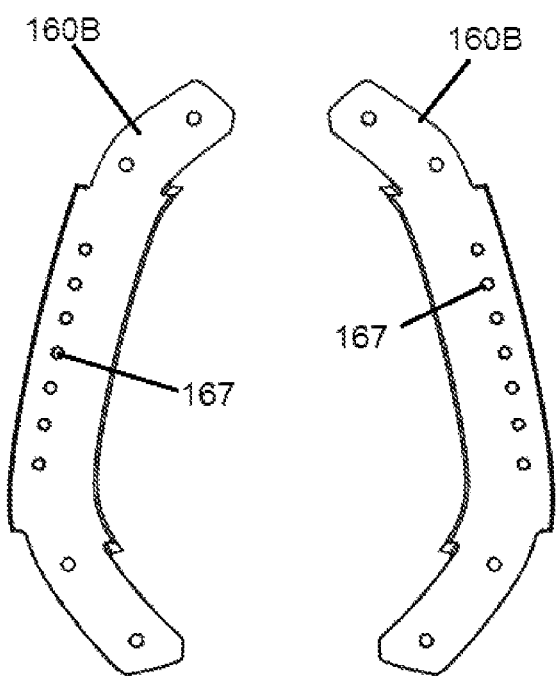
FIG. 6D is an elevational view of front sides of rear portions of a pair of outrigger assemblies as illustrated in FIG. 6A.
Figure 6E:
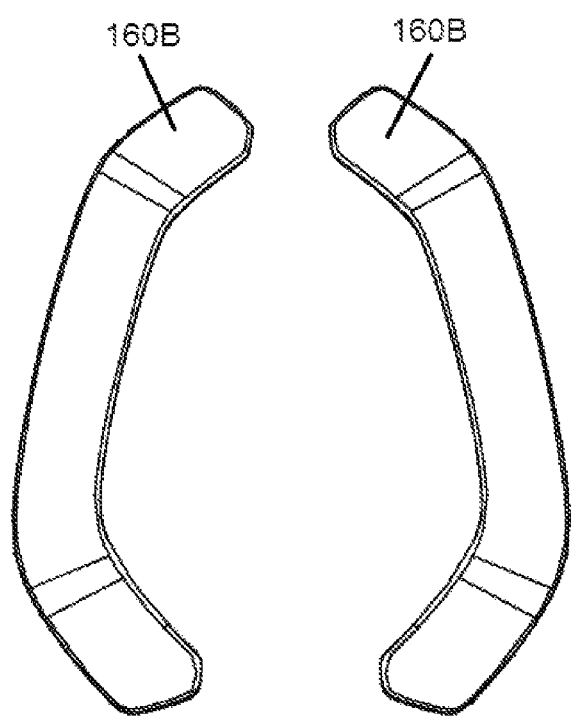
FIG. 6E is an elevational view of rear sides of rear portions of a pair of outrigger assemblies as illustrated in FIG. 6A.
Figure 7:
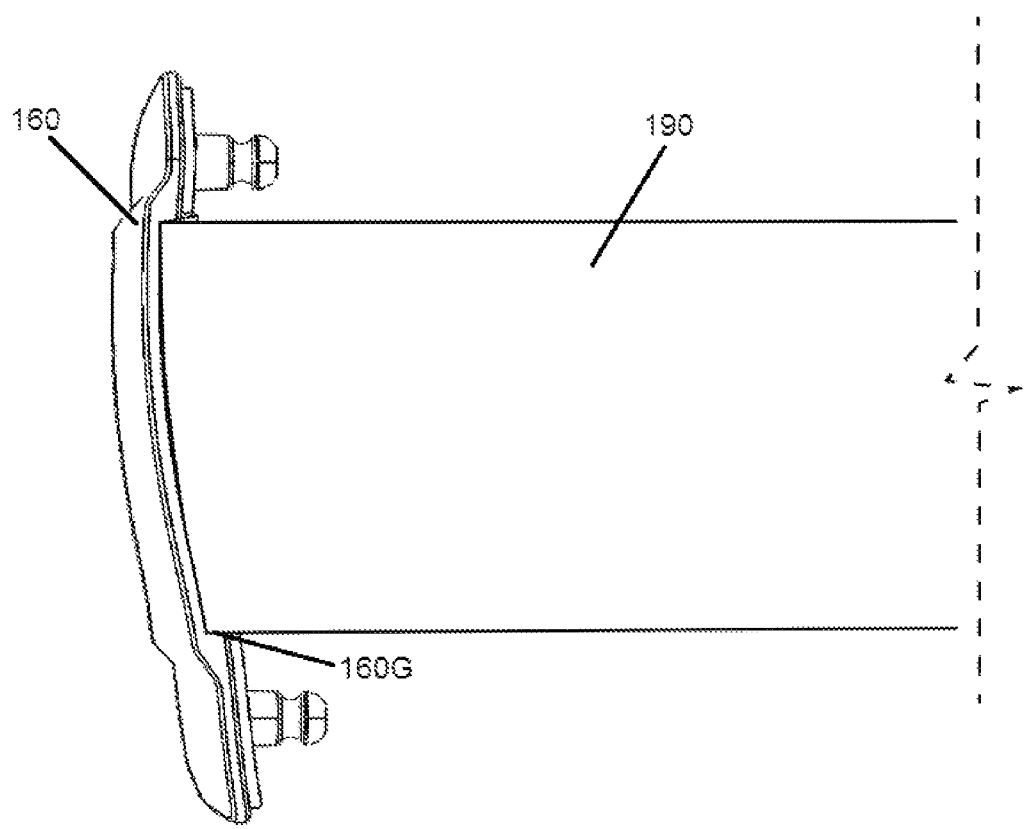
FIG. 7 illustrates attachment of a headstrap to the outrigger assembly of FIG. 6A.
Figure 11:
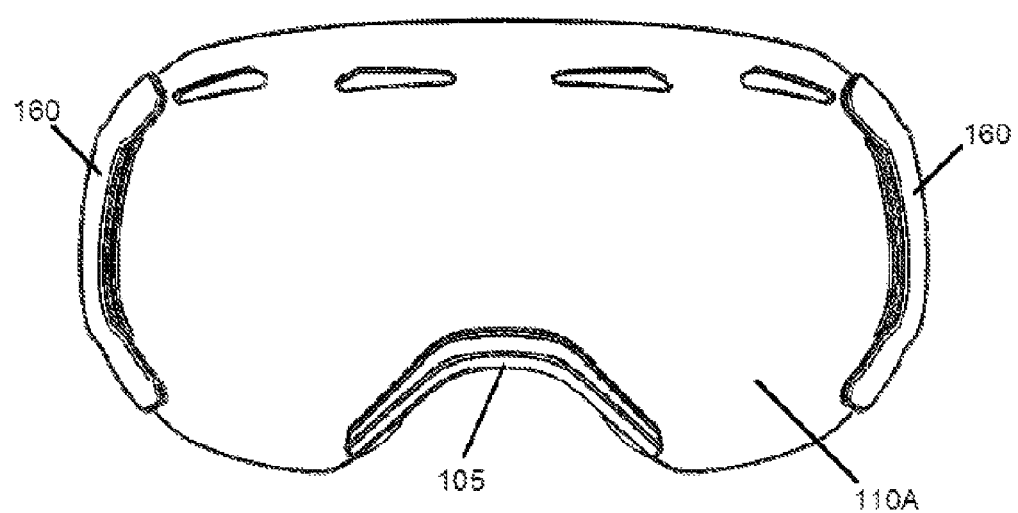
FIG. 11 is an elevational view from the front of the goggles of FIG. 1.

In some embodiments, the lens assembly 110 is removably secured to the front of the flexible body 105 with a quick change lens attachment system. The lens attachment system may be a "quick change" or "quick release" system in the sense that it allows a user to remove and replace the lens assembly 110 manually and without the use of tools in a short time period, for example, within about one minute or a few minutes. The quick change lens attachment system may allow for a wearer to swap lens assemblies 110, for example, to mount a lens assembly having a desired degree of tint appropriate for use based on the weather conditions or to replace a damaged lens assembly 110. In some embodiments, the quick change lens attachment system includes right and left side outrigger assemblies 160 (See FIGS. 6A-6E) that include posts 165 that pass through apertures 170 in the lens assembly 100 proximate edges of the lens assembly 110 and that snap into receiving columns 175 of corresponding receiving units 180 disposed in the flexible body 105. The apertures 170 in the lens assembly 110 may be positioned such that when the outrigger units 160 are in place holding the lens assembly 110 on the flexible body 105, the outrigger assemblies 160 are outside of a field of view of a wearer of the goggles 100 and are thus not visible to the wearer (See FIG. 11). In some embodiments, the receiving columns 175 are disposed in apertures 185 in the flexible body 105. The outrigger assemblies 160 may include rear portions 160A and front portions 160B. The rear portions 160A and front portions 160B may be joined together and define a gap 160G therebetween configured to receive an end of a headstrap 190 (see FIG. 7). Then ends of the headstrap 190 may be secured within the gaps 160G of the outrigger assemblies 160 with an adhesive, and/or by projections or teeth 167 on the internal surfaces of the rear portions 160A and/or front portions 160B of the outrigger assemblies 160. (See FIGS. 6A, 6C, and 6D.) In other embodiments, the lens assembly 110 may be releasably secured to the front of the flexible body with, for example, hook and loop fasteners, snaps, or other connectors having complimentary portions disposed on the lens assembly 110 and the front of the flexible body 105.

Figure 8:
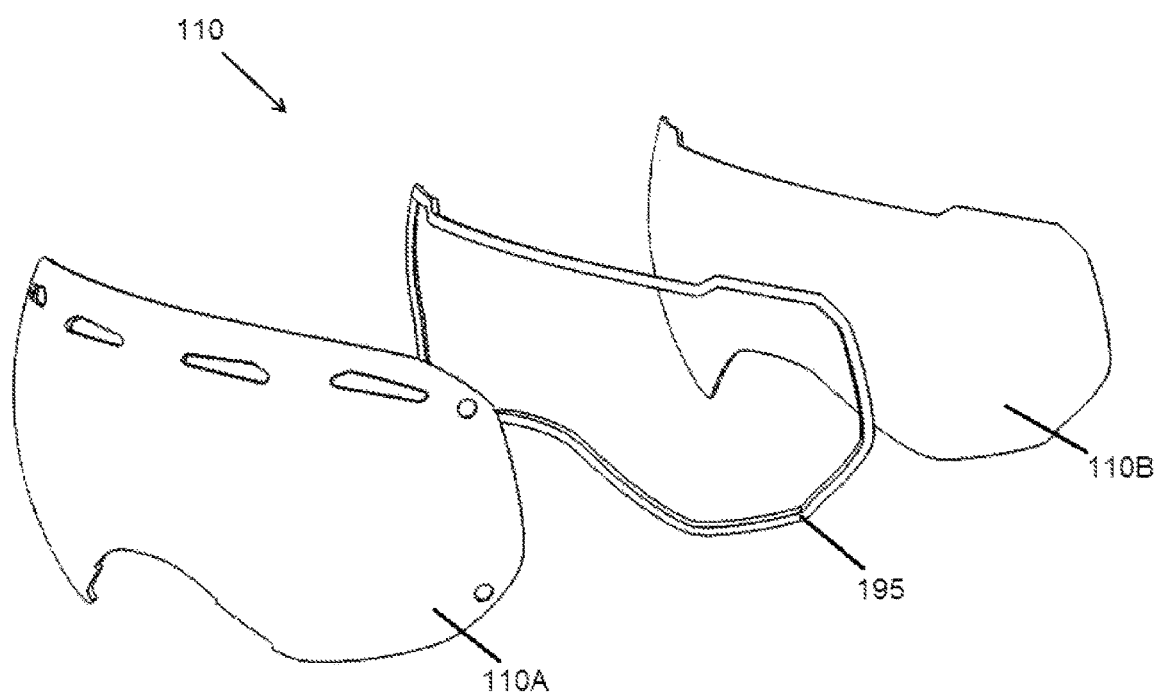
FIG. 8 is an exploded view of a lens assembly for use with the goggles of FIG. 1.

In some embodiments, as illustrated in an exploded view in FIG. 8, the lens assembly 110 is a dual lens assembly including an outer lens 110A and an inner lens 110B. The inner lens 110B is omitted from FIG. 2 for clarity. In use, the inner lens 110B is disposed closer to the face of a wearer than the outer lens 110A while the outer lens 110A is disposed forward of the inner lens 110B on the goggles. A dual lens assembly may reduce the tendency for the lens assembly 110 to fog during use by partially insulating the inner lens 110B from cold air. The inner lens 110B may be smaller than the outer lens 110A. The inner lens 110B may be secured to the outer lens 110A substantially centered within borders of the outer lens 110A. In some embodiments, the inner lens is secured to the outer lens with a gasket 195. The gasket may include a polymeric foam material and/or a rubber material. The gasket 195 may provide a spacing of between about 0.5 mm and about two mm between the inner lens 110B and the outer lens 110A. The outer and/or inner lenses 110A, 110B may be formed from clear, tinted, or colored polycarbonate, a proprionate material, or other transparent material. The outer and inner lenses 110A, 110B may be formed from different materials. In some embodiments, the inner lens 110B has a shape that conforms to an inner border 200 of the front opening 205 of the flexible body 105. When the lens assembly 110 is mounted on the flexible body 105, the thickness of the gasket 195 may cause the inner lens 110B to extend into the front opening 205 of the flexible body 105. In some embodiments, when the lens assembly 110 is mounted on the flexible body 105, the inner lens 110B and/or gasket 195 forms a seal against a portion of the inner border 200 of the front opening 205 of the flexible body 105, for example, against left and right and/or bottom sides of the inner border 200 of the front opening 205 of the flexible body 105, that discourages or prevents snow, dirt, or other debris from entering the interior of the goggles 100. Outer borders of the inner lens 110B and/or gasket 195 may be spaced from one of the top side and/or the bottom side of the inner border 200 of the front opening 205 of the flexible body 105 to allow air to flow through ventilation apertures in the outer lens 110A into the interior of the goggles.

In some embodiments, the lens assembly 110 may include one or more tabs 230 extending from a portion of the lens assembly 110, for example, from sides of the outer lens 110A. The one or more tabs 230 may facilitate removal of the lens assembly 110 from the flexible body 105 by providing an area of the lens assembly 110 that is easily gripped by a wearer so that the wearer may pull the lens assembly 110 off of the flexible body 105. The one or more tabs 230 may extend beyond an outer border of the flexible body 105 when the lens assembly 110 is mounted on the flexible body 105.

Figure 9:
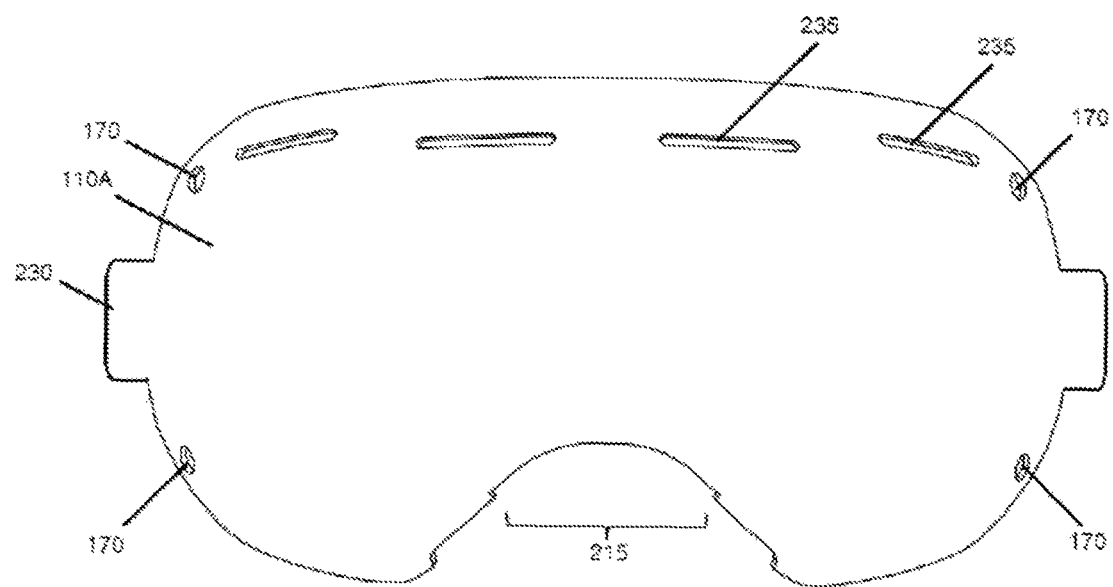
FIG. 9 is an elevational view from the front of the lens assembly of FIG. 8.
Figure 10A:
FIG. 10A is an elevational view from the rear of a retention post assembly for use with the goggles of FIG. 1.
Figure 10B:
FIG. 10B is an elevational view from the front of the retention post assembly of FIG. 10A.
Figure 10C:
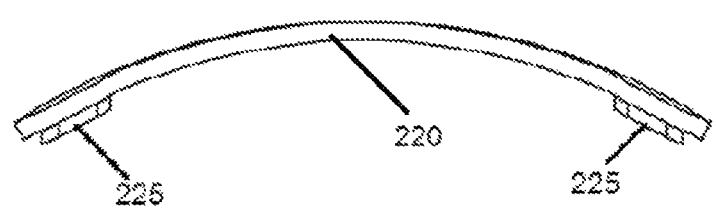
FIG. 10C is a plan view of the retention post assembly of FIG. 10A.

In some embodiments, the flexible body 105 and lens assembly 110 include features that facilitate holding the lens assembly 110 in place when mounted on the flexible body 105. One feature that facilitates holding the lens assembly 110 in place when mounted on the flexible body 105 is a groove 210 formed in an upper portion of the nose bridge section 120 of the flexible body 105. A portion of the lower edge 215 of the outer lens 110A (see FIG. 9) is shaped to fit into the groove 210 when the lens assembly 110 is mounted on the flexible body 105. The groove 210 thus holds the lower edge 215 of the outer lens 110A in place when the lens assembly 110 is mounted on the flexible body 105.

Another feature that facilitates holding the lens assembly 110 in place when mounted on the flexible body 105 is a retention post assembly 220. The retention post assembly 220 may include one or more retention posts 225 secured to a portion of the lens assembly 110, for example, proximate a border of the inner surface of the outer lens 110A. The front face 135 of the flexible body 105 includes recesses or cavities 230 that receive the one or more retention posts 225 when the lens assembly 110 is mounted on the flexible body 105. The recesses or cavities 230 hold the one or more retention posts 225, and by extension, the lens assembly 110 in place against the front face 135 of the flexible body 105. The recesses or cavities 230 in combination with the retention posts 225 provide a resistance to movement of the lens assembly 110 across the front face 135 of the flexible body 105. In FIG. 1 and FIGS. 10A-10C, the retention post assembly 220 is illustrated as a unitary body including two retention posts 225 located at an upper brow area of the goggles 100. In this embodiment, the retention post assembly 220 may be referred to an upper brow retention assembly having upper brow retention posts. In other embodiments, a greater or fewer number of retention posts 225 and complimentary recesses or cavities 230 may be provided on the lens assembly 110 and flexible body 105, respectively, than illustrated. The retention posts 225 and complimentary recesses or cavities 230 may be located in other areas of the lens assembly 110 and flexible body 105, respectively, than illustrated. The retention post assembly 220 may be formed from a plastic material adhered to the inner surface of the outer lens 110A with an adhesive, although the material of the retention post assembly 220 is not limited to any particular material and the retention post assembly 220 may be secured to the outer lens 110A by any means known in the art, for example, with one or more screws, bolts, snaps, clips, or other connectors.

In some embodiments a ridge 245 may extend from a front face 135 of the flexible body 105 (See FIG. 2). The ridge 245 may be compressed against the material of the lens assembly 110 when the lens assembly 110 is mounted on the flexible body 105, thus forming a water tight and/or air tight seal between the lens assembly 110 and the front face 135 of the flexible body 105. In some embodiments, the ridge 245 may have a substantially rectangular cross-section while in other embodiments the ridge 245 may have a substantially triangular or hemispherical cross section. In some embodiments, the ridge 245 completely circumscribes the front face 135 of the flexible body, while in other embodiments the ridge 245 is provided only on certain portions of the front face 135 of the flexible body 105, for example in areas other than the nose bridge section 120.

In some embodiments, the lens assembly 110 is the most rigid portion of the goggles 100. All other portions of the goggles 100, for example, the flexible body 105 and its components may be sufficiently flexible and compressible to conform to the shape of the face of a wearer and provide a comfortable fit. The lens assembly 110 and other portions of the goggles 100 may be sufficiently flexible to easily conform to the face of a wearer due to force applied to the goggles 100 by the headstrap 190.

The combination of the headstrap attachment, lens apertures 235, frame apertures 130 and crenels, lens assembly 110 and features maintain the lens assembly 110 in position on the flexible body 105, and headstrap 190 form an integrated system that pulls the goggles 100 against the face of a wearer. The headstrap 190, through the outriggers 160, pulls on the lens assembly 110 which is secured in place on the flexible body 105. The features that maintain the lens assembly 110 in position on the flexible body 105, for example, the groove 210 formed in the upper portion of the nose bridge section 120 of the flexible body 105 and the recesses or cavities 230 in the flexible body 105 and associated retention posts 225 disposed on the lens assembly 110 provide for the goggles 100 to deform to conform to the face of a wearer while maintaining a gap free connection between the lens assembly 110 and the flexible body 105 and between other portions of the goggle.

Embodiments of the goggles 100 may include a ventilation system. The ventilation system may facilitate reducing or eliminating fogging of the goggles 100 while in use. In some embodiments, the ventilation system includes one or more ventilation apertures 235 in the lens assembly, for example, passing through the outer lens 110A. The ventilation apertures 235 may by located proximate an upper edge of the outer lens 110A as illustrated, but may also or alternatively be located in other regions of the outer lens 110A, for example, proximate side and/or bottom borders of the outer lens 110A. Ventilation apertures may also be provided in the flexible body 105. The ventilation apertures in the flexible body 105 may comprise the apertures 130 illustrated in FIG. 4. The ventilation apertures in the flexible body 105 and/or lens assembly 110 may be sized and arranged to cause air to flow into or out of the goggles 110 at different rates on different sides of the goggles 100, for example, at a different rate through apertures on the upper side of the flexible body 105 of the goggles 100 than through apertures on the bottom side of the flexible body 105 of the goggles 100. This differential air flow may facilitate circulation of air through the goggles and reduce or eliminate fogging of the goggles 100. In some embodiments, the ventilation apertures 235 in the lens assembly 110 causes air to flow substantially tangentially across ventilation apertures in the flexible body 105, thus drawing air out of the ventilation apertures in the flexible body 105 and in through other ventilation apertures in the flexible body 105 by a venturi effect.

In some embodiments, the ventilation apertures in the flexible body 105 and/or lens assembly 110 may be covered with a mesh material 240 and/or have a mesh material 240 disposed within the apertures. The mesh material 240 may allow the passage of air through the ventilation apertures while blocking snow, dirt, or other debris. In some embodiments, the mesh material 240 includes a breathable, waterproof polymer mesh, for example, a polyurethane mesh.

Figure 12:
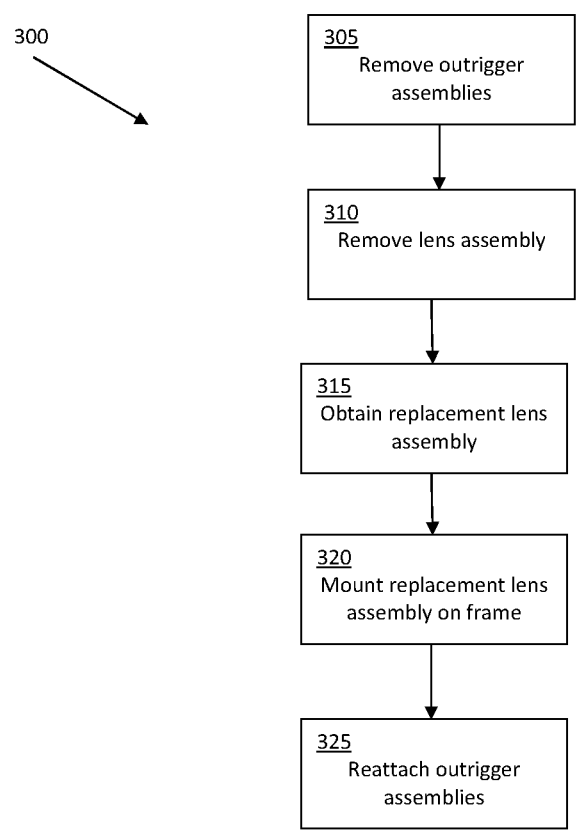
FIG. 12 is a flowchart of a method of replacing the lens assembly of a pair of goggles as disclosed herein.

A method of replacing the lens assembly 110 of the goggles 100 is illustrated in the flowchart 300 of FIG. 12. In a first act, 305 a wearer removes a first and a second outrigger assembly 160 from the goggles 100. The headstrap of the goggles 100 is attached to the outrigger assemblies 160 and is removed from the goggles along with the outrigger assemblies 160. In act 310, the lens assembly 110 is removed from the flexible body 105. A wearer may pull on one or both of the tabs 230 of the lens assembly 110 to remove the lens assembly 110 from the flexible body 105. Removing the lens assembly 110 from the flexible body 105 may include disengaging the lower edge portion 215 of the outer lens 110A from the groove 210 formed in the upper portion of the nose bridge section 120 of the flexible body 105. Removing the lens assembly 110 from the flexible body 105 may include disengaging the retention posts 225 of the retention post assembly 220 from the complimentary recesses or cavities 230 in the flexible body 105. In act 315 a replacement lens assembly 110 is obtained. In act 320 the replacement lens assembly 110 is mounted on the flexible body. Mounting the replacement lens assembly 110 on the flexible body 105 may include disposing the lower edge portion 215 of the outer lens 110A of the replacement lens assembly 110 in the groove 210 formed in the upper portion of the nose bridge section 120 of the flexible body 105. Mounting the replacement lens assembly 110 on the flexible body 105 may include engaging retention posts 225 of a retention post assembly 220 of the replacement lens assembly 110 with the complimentary recesses or cavities 230 in the flexible body 105. In act 325, the first and second outrigger assemblies 160 are reattached to the goggles 100. Reattaching the first and second outrigger assemblies 160 to the goggles 100 may involve passing posts 165 of the first and second outrigger assemblies 160 through apertures 170 in the lens assembly 110 and into receiving apertures disposed in the flexible body 105. The receiving apertures may include receiving columns 175 of receiving units 180 disposed in the flexible body 105. The posts 165 may snap into place and be removably retained in the receiving columns 175.

Having thus described several aspects of at least one embodiment of this invention, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure, and are intended to be within the scope of the invention. Accordingly, the foregoing description and drawings are by way of example only.

What is claimed is:

1. A pair of goggles comprising:
   a flexible body;
   a lens assembly; and
   a quick release system configured to removably couple the lens assembly to the flexible body, the quick release system including an outrigger assembly having a post configured to pass through an aperture in the lens assembly and snap into a receiving column of a receiving unit disposed in the flexible body to secure the lens assembly to the flexible body, the receiving column being disposed in an aperture in the flexible body.

2. The goggles of claim 1, further comprising a headstrap having an end secured to the outrigger assembly.

3. The goggles of claim 1, wherein the lens assembly is a dual lens assembly including an inner lens and an outer lens secured to the inner lens with a spacing provided between the inner lens and the outer lens.

4. The goggles of claim 3, wherein the outer lens is sandwiched between a body of the outrigger assembly and a front face of the flexible body.

5. The goggles of claim 3, wherein a gasket is disposed between a border of the inner lens and a rear surface of the outer lens.

6. The goggles of claim 5, wherein the border of the inner lens and the gasket form a seal against a portion of an inner border of the flexible body.

7. The goggles of claim 3, wherein the lens assembly includes a tab extending from a side of the outer lens.

8. The goggles of claim 7, wherein the tab extends beyond an outer border of the flexible body.

9. The goggles of claim 1, wherein the lens assembly includes a lower edge disposed in a groove formed in a nose bridge section of the flexible body.

10. The goggles of claim 1, wherein the lens assembly includes a retention post configured to engage a retention recess formed in the flexible body.

11. The goggles of claim 1, wherein the flexible body comprises a recyclable material.

12. The goggles of claim 1, further comprising a ventilation system, the ventilation system including one or more ventilation apertures in the lens assembly and one or more ventilation apertures in an upper wall of the flexible body and/or a lower wall of the flexible body.

13. The goggle of claim 12, wherein the one or more ventilation apertures in the lens assembly are configured to direct air across the one or more ventilation apertures in the upper wall of the flexible body and/or the lower wall of the flexible body to draw air in through the one or more ventilation apertures in the upper wall of the flexible body and/or the lower wall of the flexible body by a venturi effect.

14. The goggles of claim 1, further comprising a face foam gasket coupled to a rear face of the flexible body, the face foam gasket including a material softer than a material of the flexible body, the face foam gasket configured to conform to a face of a wearer of the goggles and form a seal against the face of the wearer.

15. The goggles of claim 14, wherein the face foam gasket is removably and replaceably coupled to the rear face of the flexible body.

16. The goggles of claim 1, wherein the flexible body is formed from a closed cell foam.

17. The goggles of claim 16, wherein the flexible body is more rigid at a front face thereof than at a rear face thereof.

18. The goggles of claim 1, further comprising a ridge extending from a front face of the flexible body that forms a water-tight and/or air-tight seal between the lens assembly and the front face of the flexible body.

19. The goggles of claim 1, wherein the post extends from one of an upper and a lower portion of the outrigger assembly, and the outrigger assembly further includes a second post that extends from the other of the upper and lower portion of the outrigger assembly.

20. The goggles of claim 2, wherein the outrigger assembly includes a rear portion and a front portion and the end of the headstrap is secured within a gap defined between the rear portion and the front portion.

21. The goggles of claim 2, wherein the flexible body is sufficiently flexible to conform to a face of a wearer due to force applied to the goggles by the headstrap.

22. The goggles of claim 9, wherein the lens assembly is a dual lens assembly including an inner lens and an outer lens secured to the inner lens with a spacing provided between the inner lens and the outer lens, and the lower edge is a lower edge of the outer lens.

\* \* \* \* \*

UNITED STATES PATENT AND TRADEMARK OFFICE
CERTIFICATE OF CORRECTION

PATENT NO. : 9,943,444 B2  
APPLICATION NO. : 15/147995  
DATED : April 17, 2018  
INVENTOR(S) : Matthew Kilduff et al.

Page 1 of 1

It is certified that error appears in the above-identified patent and that said Letters Patent is hereby corrected as shown below:

On the Title Page

Item [73], delete "Portal Instruments, Inc., Cambridge, MA (US)" and insert -- Bern Unlimited Inc., Kingston, MA (US) --

Signed and Sealed this  
Nineteenth Day of June, 2018

Andrei Iancu  
*Director of the United States Patent and Trademark Office*